United States Patent
Lenz

(10) Patent No.: US 6,817,223 B2
(45) Date of Patent: Nov. 16, 2004

(54) COMPACT TRIBOLOGY TESTER

(75) Inventor: James R. Lenz, Canton, MI (US)

(73) Assignee: Tecumseh Products Company, Tecumseh, MI (US)

( * ) Notice: Subject to any disclaimer, the term of this patent is extended or adjusted under 35 U.S.C. 154(b) by 0 days.

(21) Appl. No.: 10/409,467

(22) Filed: Apr. 8, 2003

(65) Prior Publication Data
US 2004/0200262 A1 Oct. 14, 2004

(51) Int. Cl.⁷ ............................................... G01N 19/02
(52) U.S. Cl. ............................ 73/10; 73/9; 73/53.05; 73/54.01; 73/866
(58) Field of Search ........................... 73/7–10, 53.05, 73/54.01, 54.02, 54.23, 54.28, 64.55, 866, 865.3, 865.6

(56) References Cited

U.S. PATENT DOCUMENTS

| | | | |
|---|---|---|---|
| 2,106,170 A | | 1/1938 | Faville ............................ 73/10 |
| 2,110,288 A | | 3/1938 | Cornell ........................... 73/10 |
| 3,033,017 A | * | 5/1962 | Whitehead ....................... 73/7 |
| 3,060,721 A | | 10/1962 | Marsh et al. .................... 73/10 |
| 3,178,928 A | | 4/1965 | Howe .............................. 73/9 |
| 3,190,109 A | | 6/1965 | Faville ........................ 73/1.89 |
| 3,221,534 A | * | 12/1965 | Alfred et al. ..................... 73/7 |
| 3,302,447 A | | 2/1967 | Mertwoy et al. ............... 73/10 |
| 3,878,112 A | * | 4/1975 | Luck et al. .................... 252/68 |
| 3,913,377 A | * | 10/1975 | Lindeman ...................... 73/10 |
| 3,939,690 A | | 2/1976 | Kuss et al. ....................... 73/9 |
| 4,064,455 A | * | 12/1977 | Hopkins et al. ............. 324/663 |
| 4,165,924 A | * | 8/1979 | Mohrman .................... 351/245 |
| 4,228,674 A | | 10/1980 | Mertwoy ....................... 73/10 |
| 4,561,784 A | * | 12/1985 | Benz et al. ..................... 374/8 |
| 4,643,021 A | * | 2/1987 | Mattout .................... 73/54.28 |
| 4,884,577 A | * | 12/1989 | Merrill ....................... 600/370 |
| 5,007,284 A | * | 4/1991 | Slone ........................... 73/120 |
| 5,020,635 A | * | 6/1991 | Lunn ......................... 184/6.18 |
| 5,052,219 A | * | 10/1991 | Fery et al. ................ 73/152.22 |
| 5,281,535 A | | 1/1994 | Wei et al. ....................... 436/6 |
| 5,388,442 A | | 2/1995 | Kumar et al. ................... 73/10 |
| 5,616,842 A | * | 4/1997 | Armengaud et al. ...... 73/152.18 |
| 5,679,883 A | | 10/1997 | Wedeven ........................ 73/10 |
| 5,874,665 A | * | 2/1999 | Larsson ..................... 73/54.28 |
| 5,955,655 A | | 9/1999 | Evans .............................. 73/7 |
| 5,969,227 A | | 10/1999 | Kenney ......................... 73/10 |
| 6,070,456 A | * | 6/2000 | Cameron et al. .......... 73/53.05 |
| 6,105,415 A | | 8/2000 | Kenney ......................... 73/10 |
| 6,145,370 A | * | 11/2000 | Evans .............................. 73/7 |
| 6,167,752 B1 | * | 1/2001 | Raffer ....................... 73/54.28 |
| 6,245,571 B1 | | 6/2001 | Roman ......................... 436/61 |
| 6,257,051 B1 | * | 7/2001 | Boyle et al. ............... 73/54.01 |
| 6,412,338 B2 | * | 7/2002 | Boyle et al. ............... 73/54.34 |

OTHER PUBLICATIONS

Opti Temp, Inc., "Combination Water Chiller/Mold Temperature Controller", Oct. 15, 2001, Available on the Internet at <http://www.optitemp.com>.*

(List continued on next page.)

Primary Examiner—Helen Kwok
Assistant Examiner—David A. Rogers
(74) Attorney, Agent, or Firm—Baker & Daniels

(57) ABSTRACT

An apparatus for testing properties of materials under operating conditions of the materials. The apparatus includes a hermetically sealed vessel in which a tribology tester is mounted. The tribology tester includes a pair of lever arms having first and second ends with the first end of each lever being pivotally connected. A spring is located between the second end of each of the lever arms with a test block assembly being mounted between the lever arms in a position between the pivotal connection and the spring. The test block assembly includes a pair of test blocks and a pin with the spring biasing the test blocks into contact with the pin. Drive means, such as a motor, is magnetically coupled to the tribology tester to rotatively drive the pin against the test blocks to test the properties of the materials.

29 Claims, 4 Drawing Sheets

OTHER PUBLICATIONS

Cubberly, William H., "SAE Dictionary of Aerospace Engineering", 1992, Society of Automotive Engineers, Inc., pp. 56.*

"Magnetic Stirrer Drives," Parr Instruments Co., Available on the Internet @<http://www.parrinst.com> Before Oct. 25, 2002.

*Friction and Wear Testing Machines to Evaluate Tomorrow's Lubricants*, H.T. Azzam, American Society of Lubrication Engineers, May 6–9, 1998.

*Testing Solid Lubricants*, H.T. Azzam, Dow Corning Corporation, at least as early as Apr. 1970.

* cited by examiner

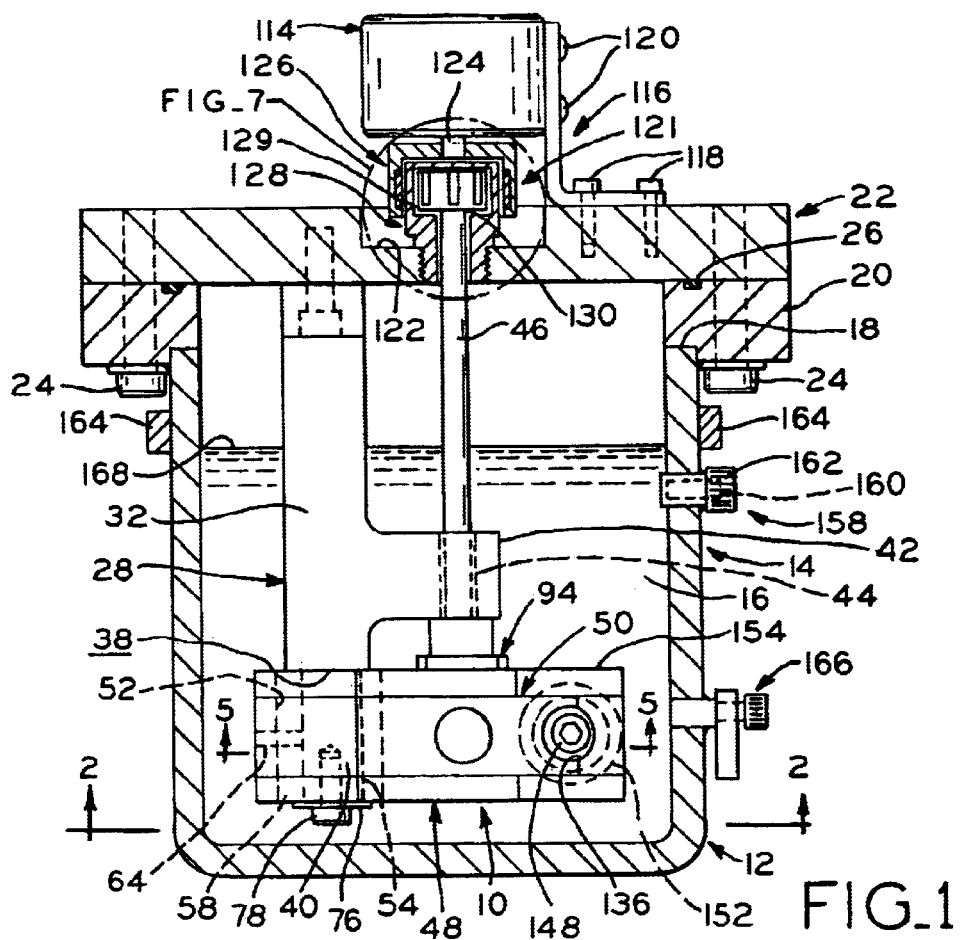
FIG_1
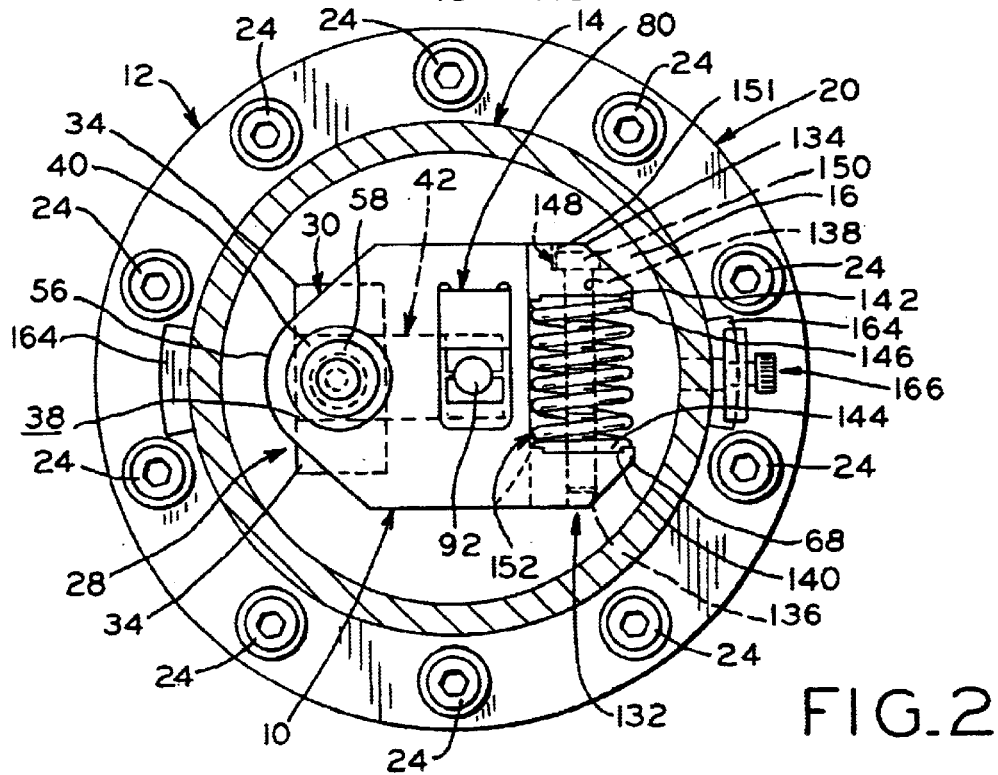
FIG_2

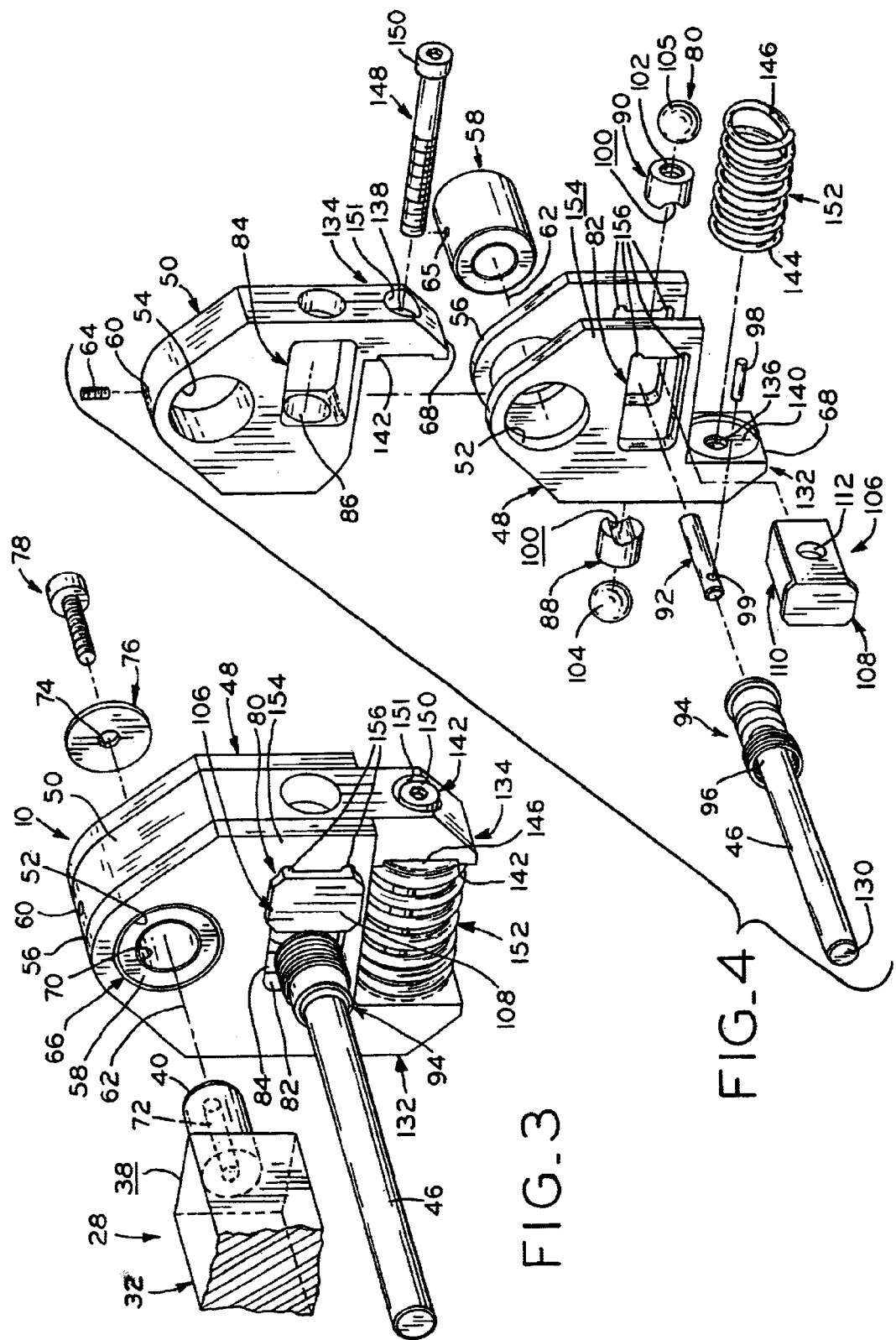
FIG._3
FIG._4

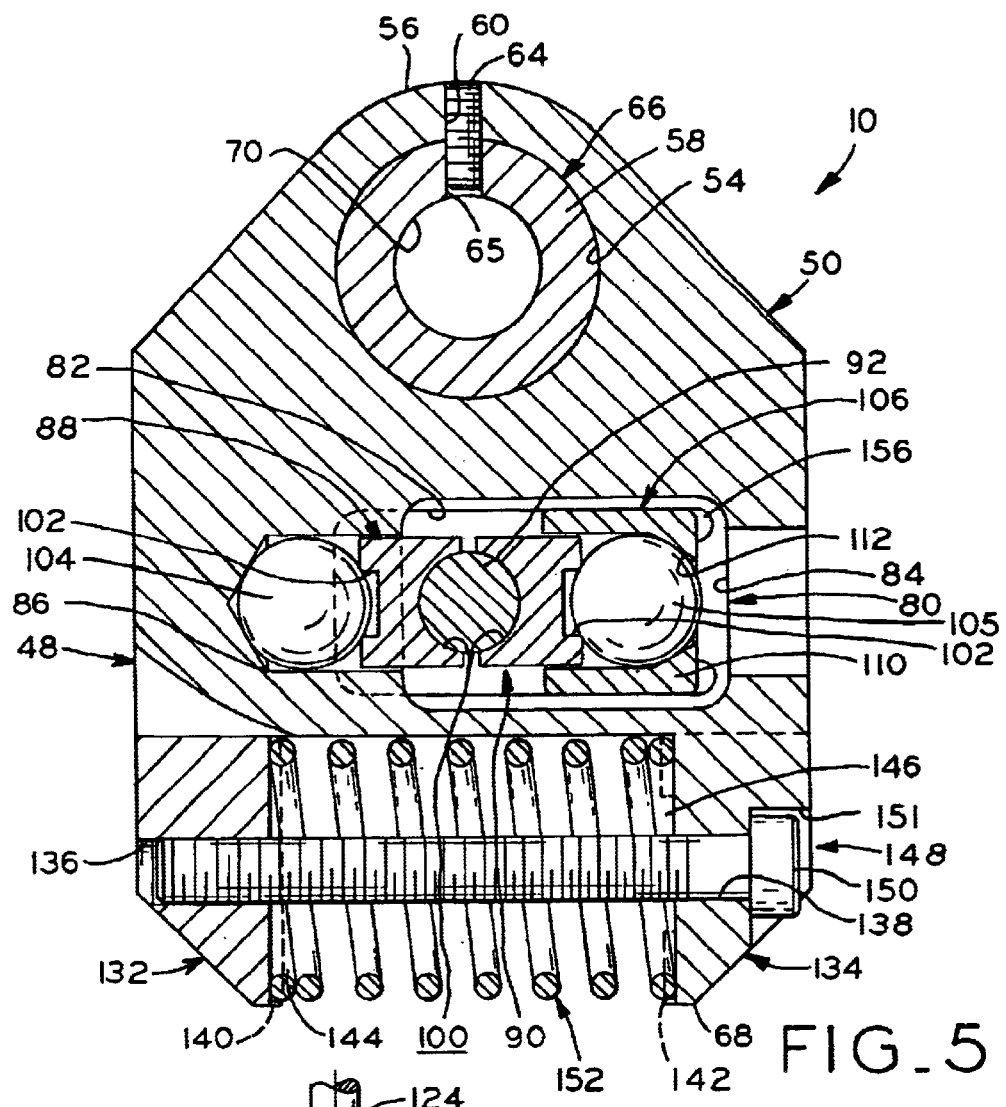
FIG_5
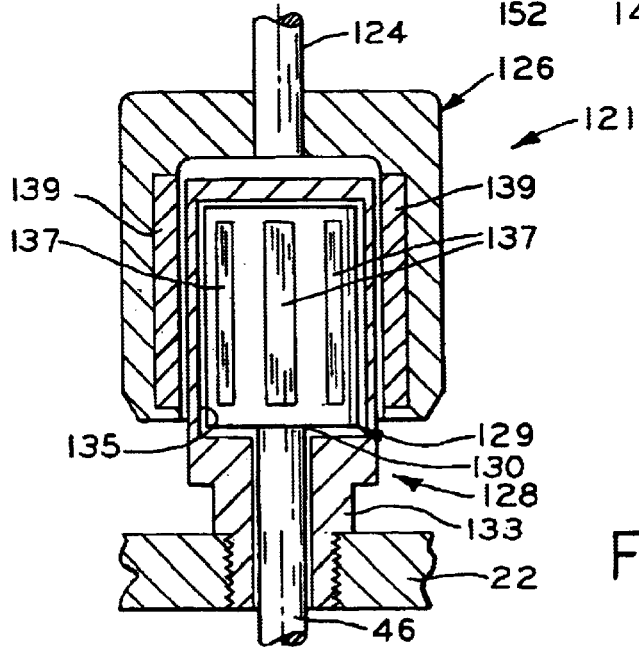
FIG_7

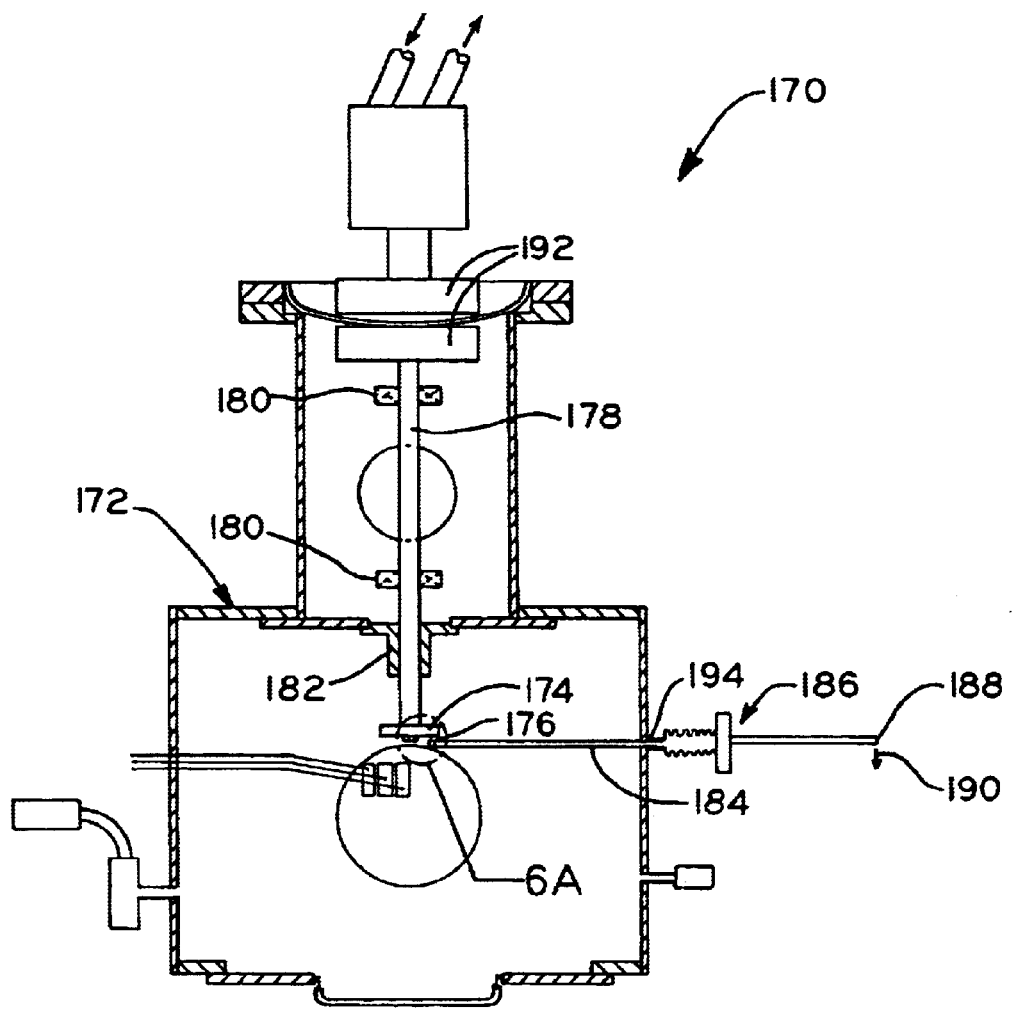
FIG_6
PRIOR ART
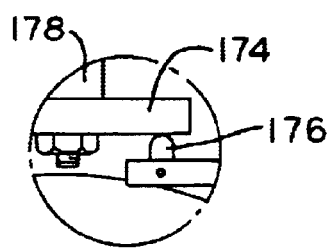
FIG_6A
PRIOR ART

COMPACT TRIBOLOGY TESTER

BACKGROUND OF THE INVENTION

The present invention relates to a compact tribology tester for testing the wear of interfacing surfaces and lubrication properties.

In general, tribology testers are used to study the design, friction, wear, and lubrication of interacting surfaces which are in relative motion. Such interfacing surfaces may include bearing surfaces, gears, or the like. There are several types of tribology testers including testers using test blocks and a rotating pin, pin-on-disk testers, four ball testers, and friction testers.

An example of the type of tester that uses test blocks and a rotating pin is described in U.S. Pat. No. 2,110,288 to Cornell and includes mounting the pin to a drive motor for rotation therewith. A pair of test blocks are supported in the tester in contact with the rotating pin. As shown in FIG. 7 of the Cornell reference, a load is applied to the test blocks and thus the pin by plugs which threadedly engage supports in which the test blocks are mounted. As the plugs are threaded into the supports, the load upon the test blocks and thus the pin is increased. The test blocks are provided with concave portions in which the pin is received so as to ensure a contact between the blocks and the pin. The position of the test blocks may be adjustable so that the contact between the test blocks and pin may be varied. The test block and pin assembly is placed into a tray filled with lubricant. The motor drives the pin to rotate against the testing blocks in the lubricant such that the wear of the material of the test blocks against the material of the pin and the properties of the lubricant can be observed.

A second type of tester 170 is illustrated herein, in FIGS. 6 and 6A, and includes pressure chamber 172 in which test specimens 174 and 176 are mounted. Pressure chamber 172 allows the environment to be a pressurized fluid rather than being exposed to ambient air or simply submersed in lubricant. Further, chamber 172 may be adapted so that the fluid may be heated. Shaft 178 is mounted in chamber 172 by bearings 180 and seal 182 with test specimen 174 mounted to one end thereof. Test specimen 176 is mounted to an internal end of movable shaft 184 of gimbal assembly 186. Shaft 184 extends through a sidewall of pressure chamber 182 requiring seal 194 between the shaft and sidewall. Hence, this tester is non-hermetic. A load is applied to external end 188 of shaft 184 in the direction of arrow 190 which in turn causes shaft 184 to pivot slightly about seal 194, and test specimen 176 to be upwardly loaded against test specimen 174. Magnetic drive assembly 192 is located at the end of shaft 178 opposite to test specimen 174 and is provided to rotatably drive shaft 178. Rotation of shaft 178 causes rotation of test specimen 174 against stationary test specimen 176.

Several problems exist with prior versions of the above-identified testers. One such problem with the pin and test block type tester of Cornell is that the pin and test block assembly is merely submersed into an open tray of lubricant. Therefore, operating conditions encountered in a pressurized vessel, such as a compressor, are not achieved.

A problem with above-identified tester 170 mounted within pressurized chamber 172 is that the maximum pressure within chamber 172 is limited due to potential leakage between specimen shaft 184 and the sidewall of chamber 172 across seal 194. Therefore, sustained high-pressure operating conditions, where pressures may reach 3000 psi, cannot be reliably reproduced. Additionally, the load is applied to test specimens 174 and 176 externally of chamber 172 via specimen shaft 184. A problem with external loading of the specimens is that a significant amount of space is required to accommodate shaft 184. Further, seal 194 may impart a force, or torque, on shaft 184 which may be a function of the internal pressure within chamber 172, for example. This force may be difficult to account for in the test results, and thus the test results may be altered.

It is desired to provide a self-contained, compact tribology tester for testing the wear of interfacing surfaces and properties of the lubricant in a compressor under hermetic operating conditions.

SUMMARY OF THE INVENTION

The present invention provides a compact tribology tester device which is located within a hermetically sealed vessel. The device includes a test pin which slidably engages a pair of test blocks, each block being mounted at the end of a lever arm. The lever arms are pivotally attached, with a spring located between the arms. The spring creates a force which, through the blocks, is exerted on the pin.

The pin is mechanically coupled to a rotating shaft mounted in the vessel. The shaft is magnetically coupled to drive means, such as a motor, located outside of the vessel. The testing device is mounted on a support which is secured in the vessel such that the pin shaft of the device is aligned with the motor. Operation of the motor rotatably drives the shaft to cause rotation of the pin between the blocks. The temperature and pressure of a testing medium, such as an oil and refrigerant mixture, located in the vessel can be varied in order to simulate the operating conditions of a hermetic compressor so that the wear between interfacing surfaces and properties of the lubricant during operation may be analyzed.

Particular embodiments of the present invention provide a testing apparatus including a hermetically sealed vessel in which a tribology tester is completely mounted. A drive means is located externally of the hermetically sealed vessel and operatively engaging the tribology tester.

Particular embodiments of the present invention further provide a testing apparatus having a hermetically sealed vessel, and a tribology tester mounted completely therein. A drive means is located externally of the hermetically sealed vessel. A tribology tester is mounted completely within the hermetically sealed vessel. The tribology tester includes a test block assembly having a block and a pin, at least one of which is a test specimen. The drive means is operatively engaged with the pin to drive the pin. The tribology tester also includes means for loading the block against the pin which is located completely within the hermetically sealed vessel.

Particular embodiments of the present invention also provide a tribology tester having a test block assembly including a pair of blocks and a pin. The test blocks are located on radially opposite sides of the pin. The test block assembly further includes at least one test specimen where at least one of a test block and the pin is the test specimen. The tribology tester also includes means for applying a substantially equivalent and constant load between each block and the pin during wearing of the test specimen.

Particular embodiments of the present invention also provide a method of testing material properties including selecting at least one test specimen of a material to be tested, the test specimen being a block or a rotating pin; mounting a tester into a vessel; placing the block and the rotating pin in engagement; applying a load between the block and the rotating pin; hermetically sealing the vessel; filling the hermetically sealed vessel with a pressurized fluid test medium; and rotating the pin with drive means located outside the hermetically sealed vessel.

One advantage of the present invention is that more realistic operating conditions can be simulated with the tribology tester device being located in a hermetically sealed vessel.

Additionally, an advantage of the present invention is that by providing the tribology tester within a hermetically sealed vessel, tribology testing under very high pressures, such as those experienced with refrigerants such as, for example, carbon dioxide, may be achieved.

BRIEF DESCRIPTION OF THE DRAWINGS

The above-mentioned and other features and objects of this invention, and the manner of attaining them, will become more apparent when the invention itself will be better understood by reference to the following description of an embodiment of the invention taken in conjunction with the accompanying drawings, wherein:

FIG. 1 is a partially sectioned side view of a tribology tester device mounted in a hermetically sealed vessel in accordance with the present invention;

FIG. 2 is a sectional view of FIG. 1 taken along line 2—2;

FIG. 3 is a partially-exploded, perspective view of the tribology tester device and support of FIG. 1;

FIG. 4 is an exploded perspective view of the tribology tester device of FIG. 1;

FIG. 5 is a sectional view of the tribology tester device of FIG. 1 taken along line 5—5;

FIG. 6 is a partially sectioned view of a prior art tribology tester;

FIG. 6A is an enlarged view of circled area 6A of FIG. 6, showing the contact between test specimens of the tribology tester; and FIG. 7 is an enlarged view of circled area 7 of FIG. 1, showing the magnetic coupling between drive means and the tribology tester.

Corresponding reference characters indicate corresponding parts throughout the several views. Although the drawings represent an embodiment of the present invention, the drawings are not necessarily to scale and certain features may be exaggerated in order to better illustrate and explain the present invention.

DETAILED DESCRIPTION OF THE INVENTION

Referring to FIGS. 1 and 2, compact tribology tester device 10 is mounted in vessel 12 and is used to determine the wear of materials and test the properties of lubricants used in a hermetic compressor, for example. Vessel 12 is hermetically sealed, meaning that there are no moving components passing through the wall of the vessel which would require seals across which fluid leakage may occur. The pressure and temperature inside the vessel can be manipulated to simulate the operating conditions of the end product, including a compressor, for example.

Hermetically sealed vessel 12 includes a main body portion 14 having cavity 16 defined therein in which tribology tester device 10 is located. Hermetically sealed vessel 12 may be constructed from any suitable material, including, for example, iron, steel, aluminum, or the like, able to withstand high operating pressures. Secured about the periphery of open end 18 of main body portion 14 is mounting flange 20. End cap 22 of hermetically sealed vessel 12 engages mounting flange 20, being aligned therewith such that a plurality of fasteners 24 secure end cap 22 to main body portion 14. Seal 26 is located between mounting flange 20 and end cap 22 to hermetically seal cavity 16.

Tribology tester 10 is mounted completely within hermetically sealed vessel 12. Mounting support 28 is provided with substantially rectangular base 30 from which substantially rectangular post 32 (FIGS. 1, 2, and 3) extends. Base 30 is provided with fastening portions 34 through which fasteners 36 extend to secure mounting support 28 to end cap 22 of hermetically sealed vessel 12. Extending downwardly from lower surface 38 of post 32 is substantially cylindrical stem 40 which engages tribology tester device 10. Extending substantially perpendicularly from post 32 is arm 42 with aperture 44 passing therethrough in which drive shaft 46 is rotatably received. Arm 42 is positioned along post 32 at a point below device 10 and along shaft 46 to support shaft 46 in a substantially vertical orientation.

Referring to FIGS. 3, 4, and 5, tribology tester device 10 includes a pair of arms 48 and 50. First arm 48 is substantially U-shaped to receive solid, second arm 50 such that the outer periphery of arms 48 and 50 substantially align in a closed position. Arms 48 and 50 are provided with apertures 52 and 54, respectively, located near first end 56 of the arms. When first arm 48 and second arm 50 are assembled, apertures 52 and 54 align to receive bushing 58. Aperture 60 is provided in second arm 50, extending substantially perpendicularly to axis 62 of bushing 58, to receive fastener 64 which engages aperture 65 in bushing 58. By securing bushing 58 within aperture 54 of arm 50, rotation of bushing 58 in aperture 54 and rotation of second arm 50 about bushing 58 is prevented. With bushing 58 in place, arms 48 and 50 are pivotally connected at 66 such that arm 48 is able to pivot about bushing 58 to open and close the distance between second end 68 of the arms during assembly, for example.

Bushing 58 is provided with substantially cylindrical aperture 70 extending through the length thereof and sized to receive cylindrical stem 40 of support 28 as shown in FIGS. 1, 2 and 3. Stem 40 is provided with aperture 72 to which aperture 74 in washer 76 is aligned. Fastener 78 engages both washer 76 and stem 40 to secure tribology tester device 10 to support 28.

Mounted between arms 48 and 50 of tribology tester 10 is test block assembly 80. First and second arms 48 and 50 are provided with openings 82 and 84, respectively, which become aligned when arms 48 and 50 are assembled and closed relative to one another. Second arm 50 is also provided with cavity 86 which together with openings 82 and 84 receive test block assembly 80.

As shown in FIGS. 4 and 5, test block assembly 80 includes at least one test specimen. The test specimens include a pair of test blocks 88 and 90 and test pin 92. The materials of blocks 88 and 90 or of pin 92 may be already used in, for example, a hermetic compressor or being tested for potential use in a hermetic compressor. Any combination of new materials or materials already in use may be analyzed. Further, the inventive tribology tester may also be used for testing new or existing combinations of oil and refrigerant under temperatures and pressures associated with anticipated operating conditions, with new or existing test block assembly materials as the test specimen(s).

Test pin 92 is supported in its position between test blocks 88 and 90 by shaft 46. Pin 92 is secured in chuck 94 mounted to end 96 of drive shaft 46 by pin 98. Blocks 88 and 90 are each provided with concave surface 100 which, when assembled with pin 92, surroundingly engages a portion of the pin's outer surface. Located on the opposite side of each test block 88 and 90 is seat 102 in which one ball 104 and 105 is respectively received. Referring to FIG. 5, a first ball 104 is located in cavity 86 formed in second arm 50. The second ball 105 is located in mounting block 106 having capped end 108 and body portion 110 extending therefrom. Body portion 110 extends a distance away from capped end 108 substantially equal to that of the thickness of assembled arms 48 and 50 and has substantially U-shaped cross section. Located in body portion 110 is conical surface 112 which forms a seat for second ball 105.

Tribology tester 10 is operated by any suitable drive means. One such drive means includes drive motor 114 mounted to the outer surface of end cap 22 by any suitable method. Motor 114 is illustrated in FIG. 1 as being mounted to end cap 22 by L-shaped bracket 116. L-shaped bracket 116 is secured to end cap 22 by fasteners 118 and to drive motor 114 by fasteners 120. Motor 114 is magnetically linked to shaft 46 to induce rotation thereof by couple 121 which is at least partially positioned in cavity 122 defined in end cap 22, in alignment with shaft 46. Any suitable type of magnetic couple 121 may be used to drivingly link shaft 46 and output shaft 124 of motor 114. One particular type of magnetic couple may be any of the magnetic drives manufactured by Parr Instruments in Moline, Ill. The model number of magnetic couple 121 used with the present invention is A2160HC. This type of magnetic couple includes a stirring device which is removed and replaced by shaft 46. Referring to FIGS. 1 and 7, magnetic couple 121 is provided with output shaft 124 having a magnetic member such as driving member 126 being secured the end thereof. Driving member 126 is aligned with, and receives at least a portion of, non-rotating housing member 128 which is threadedly secured in end cap 22. The threaded engagement between non-rotating housing member 128 and end cap 22 is hermetically sealed. Cylindrical member 129 is located at end 130 of drive shaft 46 and is secured thereto using any suitable method including threaded engagement. Shaft 46 extends through opening 131 in neck portion 133 of non-rotating housing member 128 with cylindrical member 129 being positioned in cavity 135. A plurality of magnets 137 are mounted on cylindrical member 129 and form a magnetic couple with magnets 139 mounted to driving member 126. Operation of motor 114 causes rotation of output shaft 124 and thus driving member 126 and magnets 139. Rotation of driving member 126 induces rotation of cylindrical member 129 due to the magnetic coupling formed between magnets 137 and 139, which in turn causes drive shaft 46 and thus pin 92 to rotate.

Alternative drive means may be used to operate tribology tester 10 including a belt or a set of gears. For example, a pulley may be mounted to the end of output shaft 124 being operatively connected to a motor by a belt. Operation of the motor drives the belt, which induces rotation of the pulley and thus shaft 124. Output shaft 124 may also be driven through a gear set which would drivingly link shaft 124 and a motor.

Referring to FIGS. 4 and 5, each arm 48 and 50 is provided at second end 68 with claw-like extensions 132 and 134 having respective apertures 136 and 138 extending therethrough. Claw-like extensions 132 and 134 include recessed portions 140 and 142 which are sized to receive ends 144 and 146 of spring 152. Apertures 136 and 138 extend entirely through extensions 132 and 134 and receive fastener 148 which may be any suitable type of fastener including a threaded, socket-head cap screw. Fastener 148 extends through aperture 138 and spring 152 engaging threaded aperture 136. Head 150 of fastener 148 is located in cutout portion 151 which is provided to recess fastener head 150 in claw-like extension 134. Fastener 148 is threaded into aperture 136 to keep claw-like extensions 132 and 134 of arms 48 and 50 together against the bias of spring 152. When fastener 148 is tightened, being threaded into aperture 136, claw-like extensions 132 and 134 are drawn closer together and the load on the test specimens is lessened until a minimal amount of force is applied thereto, thus allowing the specimens to be removed and replaced. A load is applied to test pin 92 and test blocks 88 and 90 by means including spring 152, arms 48 and 50, balls 104 and 105, and fastener 148. Spring 152 is located between second end 68 of arms 48 and 50 to exert a force on balls 104 and 105, and thus test blocks 88 and 90 and test pin 92. The amount of force is directly related to the compression of spring 152. The load applied by test blocks 88 and 90 is substantially equivalent on radially opposite sides of test pin 92. Further, as test blocks 88 and 90 or test pin 92 wear, the load applied by spring 152 remains substantially constant.

An alternative embodiment of tribology tester 10 may include pivotally connecting arms 48 and 50 at a midpoint of each arm, the arms forming an X-shape, like scissors, with the spring being located between first ends of the lever arms and the test block assembly being located between the second, opposite ends of the lever arms.

In assembly of tribology tester 10, second arm 50 is positioned within U-shaped arm 48 such that apertures 52 and 54 align. Bushing 58 is received in apertures 52 and 54 to pivotally connect arms 48 and 50. Fastener 64 is threadedly received in apertures 60 and 65 to secure bushing 58 in position in arm 50. Spring 152 is installed between second end 68 of arms 48 and 50 with each end of spring 152 being interference fitted onto one of spring mounts 144 and 146. The force of spring 152 causes arms 48 and 50 to pivot away from each other.

In preparation for testing, test block assembly 80 is received in assembled arms 48 and 50 between bushing 58 and spring 152. Arms 48 and 50 are pivoted toward one another as fastener 148 is tightened against the bias of spring 152, compressing spring 152. Test block assembly 80 is mounted in arm openings 82 and 84 with a first ball 104 being placed in cavity 86 in a seated position against the back surface of the cavity. Test block 88 engages ball 104, with ball 104 being seated in seat 102. A portion of test block 88 extends from cavity 86 into openings 82 and 84. The second ball 105 is positioned within mounting block 106, the second ball 105 being seated on conical surface 112. At least a portion of test block 90 is then positioned in mounting block 106 with seat 102 seated against ball 105. Mounting block 106, with ball 105 and block 90 positioned therein, is then inserted into aligned openings 82 and 84 until capped end 108 of mounting block 106 comes into contact with outer surface 154 of arm 48.

Referring to FIGS. 1 and 3, with test block assembly 80 assembled with arms 48 and 50, the assembled tribology tester 10 is mounted to support 28 which is fastened to end cap 22 of vessel 12 by fasteners 36. Shaft 46 is mounted in support 28 prior to tribology tester 10 being assembly with support 28, thus allowing pin 92 to engage test block assembly 80 at the same time. Chuck 94 is part of shaft 46 which is designed to receive test pin 92, secured therein by pin 98 inserted into both chuck 94 and aperture 99 in pin 92. Shaft 46 is inserted into aperture 44 in arm 42 of support 28 and cylindrical member 129 assembled in magnetic couple 121 is secured to upper end 130 thereof. Tribology tester 10 is then assembled to support 28 with concave portions 100 of blocks 88 and 90 engaging the outer surface of pin 92 and stem 40 passing through aperture 20 in bushing 58 until bushing 58 contacts lower surface 38 of post 32. Washer 76 is placed against bushing 58 and fastener 78 threadedly engages stem 40, securing tester 10 to support 28.

Fastener 148 is released, being loosened to allow spring 152 to exert the desired force on the test specimens. The force is exerted on arms 48 and 50 by spring 152 in an outward direction which acts on extensions 132 and 134 of arms 48 and 50, causing arms 48 and 50 to move away from one another. First arm 48 acts against U-shaped portion 110 of mounting block 106 in the direction of pin 92. The force is transferred to ball 105 in mounting block 106, test block 90, and the outer surface of test pin 92. Additionally, outward movement of second arm 50 applies a force against ball 104 in cavity 86 in the direction of pin 92, against test block 88, and thus against test pin 92. The forces acting on pin 92 by blocks 88 and 90 simulate the amount of pressure between interfacing surfaces in a hermetic compressor, for example.

Hermetically sealed vessel end cap 22 is then secured to main body portion 14 of vessel 12 by fasteners 24 such that tester 10 and support 28 are lowered into cavity 16. Vessel 12 is then charged with fluid at the require temperature and pressure until fluid line 168 (FIG. 1) is located at least above tribology tester 10. Drive motor 114 is mounted in cavity 122 in end cap 22 using L-shaped bracket 116 with driving member 126 aligned with non-rotating housing member 128. Alternatively, as discussed above, other methods of driving shaft 124 may be used in place of motor 114 including a belt or gear driven method. In the illustrated embodiment, motor 114 is operated causing rotation of shaft 46 through driving member 126 and cylindrical member 129 which in turn causes rotation of pin 92 against concave surface 100 of blocks 88 and 90.

In order to remove and replace test blocks 88, 90, and pin 92, pressure within vessel 12 is relieved. Fasteners 24 are unbolted to separate end cap 22 from main body portion 14 of vessel 12. Fastener 148 is tightened to unload test block assembly 80 and test pin 92. Bolt 78 and washer 76 are removed and tribology device 10 is lowered off of stem 40. Test pin 92 remains secured to shaft 46 and test block assembly 80 is removed with device 10. Opening 82 in arm 48 is also provided with cutout portions 156 in which an object such as a screwdriver may be inserted to pry mounting block 106 out of its assembled position. By removing mounting block 106, test blocks 88 and 90 can be removed and replaced with new pair of test blocks 88 and 90 which are, for example, unused, or of a different material. Test pin 92 may also be removed and replaced in shaft 46. Tribology tester 10 is then reinstalled in the same manner described above.

The conditions within hermetically sealed vessel 12 are predetermined such that the lubrication, pressure, and temperature are substantially similar to those in the end product, including a hermetic compressor, for example. Vessel 12 may be filled with a testing medium such as, for example, a refrigerant and oil mixture, through any suitable means including sealable port 158 (FIGS. 1 and 2). The test medium may also be evacuated from the vessel through port 158. Port 158 may be a tube welded into vessel 12 and having valve 160 located therein with the valve being of any suitable type including a Schrader valve. End cap 162 may also be provided to further seal port 158 when not in use.

The temperature and pressure conditions within vessel 12 may be set or altered using any suitable means including providing a plurality of electric heater elements 164 and pressure regulator 166. Heater elements 164 and pressure regulator 166 may be of any suitable type well known in the art. Heater elements 164 and pressure regulator 166 may be electrically linked to a control box (not shown) which would control operation of both devices. Heater elements 164 are illustrated as being located against the external wall of vessel 12, however, the heating element may also be located inside the vessel. Any suitable number of heater elements 164 may be provided to control the internal temperature of vessel 12. Pressure regulator 166 is mounted in vessel 12 by a threaded connection, for example, and is provided to control the internal pressure of the vessel. Pressure regulator 166 and port 158 are illustrated as being individual components, however, they may also be integrally formed.

In operation, pressure regulator 166 is set to a predetermined pressure which is monitored by the control box and test operator. If the pressure within vessel 12 becomes too high, regulator 166 opens, allowing a portion of the gas in the vessel to escape, thereby reducing the pressure therein. If the pressure within vessel 12 drops below the predetermined value, the control box is altered by the test operator and vessel 12 may be charged with gas through port 158 to increase the pressure therein. Therefore, as tribology tester device 10 operates in hermetically sealed vessel 12, testing of bearing surfaces in an environment simulating operating conditions of the hermetic compressor can be more accurately analyzed.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A testing apparatus comprising:
   a hermetically sealed vessel;
   drive means located externally of said hermetically sealed vessel; and
   a tribology tester mounted completely within said hermetically sealed vessel, said tribology tester comprising,
      a test block assembly comprising a block and a pin, said drive means operatively engaged with said pin, said pin rotatable driven by said means, said test block assembly including at least one test specimen, at least one of said block and said pin being said test specimen, and
      means for loading said block against said pin, said means located completely within said hermetically sealed vessel, said means for loading including a pair of lever arms, said lever arms pivotally connected, said means for loading further including a spring located between said lever arms, said spring biasing said block into contact with said pin.

2. The apparatus of claim 1, wherein said drive means and said pin are magnetically coupled.

3. The apparatus of claim 1, wherein said drive means is a motor.

4. The apparatus of claim 1, further comprising a support having two ends, one of said ends secured to said hermetically sealed vessel, said tribology tester secured to the other of said ends.

5. The apparatus of claim 1, wherein said means for loading includes a pair of lever arms, said lever arms pivotally connected.

6. The apparatus of claim 1, wherein said means for loading further includes a ball located between one of said lever arms and said block.

7. The apparatus of claim 1, wherein said means for loading further includes a fastener, said fastener engaging each of said lever arms, said arms drawn together against the bias of said spring.

8. The apparatus of claim 1, wherein each said lever arm has a first and second end, said first end of one of said lever arms pivotally connected to said first end of said other of said lever arms, said spring located between said second end of said lever arms.

9. The apparatus of claim 8, wherein said test block assembly is positioned between said spring and said pivotal connection between said lever arms.

10. The apparatus of claim 1, wherein said test block assembly includes a pair of blocks, each bearing on said pin.

11. The apparatus of claim 1, wherein a fluid test medium is provided in said hermetically sealed vessel.

12. The apparatus of claim 11, wherein said test medium is a refrigerant and oil mixture having a selected temperature and pressure, said selected temperature and pressure simulating operating conditions of a hermetic compressor.

13. A tribology tester comprising:
a test block assembly comprising a pair of blocks and a pin, said test blocks located on radially opposite sides of said pin, said test block assembly including at least one test specimen, at least one of a said test block and said pin being said test specimen and
means for applying a substantially equivalent and constant load between each said block and said pin during wearing of said test specimen
wherein said means for loading includes a pair of lever arms, said lever arms pivotally connected and wherein said means for loading further includes a spring located between said lever arms, said spring biasing said blocks into contact with said pin.

14. The tribology tester of claim 13, wherein said means for loading further includes a ball located between each of said lever arms and said blocks.

15. The tribology tester of claim 13, wherein said means for loading further includes a fastener, said fastener engaging each of said lever arms, said arms drawn together against the bias of said spring.

16. The tribology tester of claim 13, wherein each said lever arm has a first and second end, said first end of one of said lever arms pivotally connected to said first end of said other of said lever arms, said spring located between said second end of said lever arms.

17. The tribology tester of claim 16, wherein said test block assembly is positioned between said spring and said pivotal connection between said lever arms.

18. The tribology tester of claim 13, wherein each said block is mounted on a different one of said lever arms, each said block engaging said rotating pin.

19. The tribology tester of claim 18, wherein each of said blocks includes a concave portion which is in engagement with the cylindrical surface of said rotating pin.

20. A testing apparatus comprising:
a hermetically sealed vessel;
a tribology tester mounted completely within said hermetically sealed vessel; and
drive means located externally of said hermetically sealed vessel, said drive means operatively engaging said tribology tester;
wherein said tribology tester includes a pair of lever arms, each said lever arm has a first and second end, said first end of one of said lever arms pivotally connected to said first end of said other of said lever arms.

21. The apparatus of claim 20, further comprising a test medium located in said hermetically sealed vessel, said test medium having a selected temperature and pressure, said selected temperature and pressure simulating operating conditions of a hermetic compressor.

22. The apparatus of claim 20, wherein said test medium is a refrigerant and oil mixture.

23. The apparatus of claim 20, wherein said drive means is magnetically coupled to said tribology tester.

24. The apparatus of claim 20, wherein said drive means is a motor.

25. The apparatus of claim 20, further comprising a support having two ends, one of said ends secured to said hermetically sealed vessel, said tribology tester secured to the other of said ends.

26. The apparatus of claim 20, further comprising a test block assembly mounted between said lever arms, said test block assembly including a block and a pin, at least one of which is a test specimen.

27. The apparatus of claim 20, wherein said drive means is operatively coupled to said pin, said pin rotatively driven by said drive means against said block.

28. A testing apparatus comprising:
a hermetically sealed vessel;
a tribology tester mounted completely within said hermetically sealed vessel; and
drive means located externally of said hermetically sealed vessel, said drive means operatively engaging said tribology tester;
wherein said tribology tester includes; a pair of lever arms, said lever arms pivotally connected; a test block assembly mounted between said lever arms, said test block assembly including a block and a pin, at least one of which is a test specimen; and
a spring located between said lever arms, said spring biasing said block into contact with said pin.

29. The apparatus of claim 28, wherein said test block assembly is positioned between said spring and the pivotal connection between said lever arms.

* * * * *

UNITED STATES PATENT AND TRADEMARK OFFICE
CERTIFICATE OF CORRECTION

PATENT NO. : 6,817,223 B2
DATED : November 16, 2004
INVENTOR(S) : James R. Lenz

It is certified that error appears in the above-identified patent and that said Letters Patent is hereby corrected as shown below:

<u>Column 8,</u>
Line 49, delete "rotatable" and insert -- rotatably --.

Signed and Sealed this

First Day of February, 2005

JON W. DUDAS
*Director of the United States Patent and Trademark Office*